United States Patent [19]

Shabalin et al.

[11] Patent Number: 5,366,899
[45] Date of Patent: Nov. 22, 1994

[54] METHODS OF DIAGNOSING COMPLICATED UROLITHIASIS AND PREDICTING UROLITHIASIS

[75] Inventors: Vladimir N. Shabalin, ulitsa B. Galushkina, 3, korpus 1, kv. 21, Moscow; Svetlana N. Shatokhina, prospekt Mira, 70, kv. 76, Moscow; Valery V. Dutov, Moscow; Margarita F. Trapeznikova, Moscow; Andrei P. Morozov, Moscow; Andrei N. Mitroshnikov, Moscow; Leonid G. Makushin, Moscow; Sergei A. Yakovlev, Mytischi, all of Russian Federation

[73] Assignees: Vladimir N. Shabalin; Svetlana N. Shatokhina, both of Moscow,

[21] Appl. No.: 119,254

[22] Filed: Sep. 9, 1993

Related U.S. Application Data

[63] Continuation of Ser. No. 895,324, Jun. 8, 1992.

[30] Foreign Application Priority Data

Aug. 8, 1990 [SU] U.S.S.R. ............... 4858034
Oct. 11, 1990 [SU] U.S.S.R. ............... 4873890

[51] Int. Cl.$^5$ ............................................. G01N 33/493
[52] U.S. Cl. ................................... 436/88; 436/4; 436/811; 424/2
[58] Field of Search ................ 436/4, 86-88, 436/811; 424/2

[56] References Cited

U.S. PATENT DOCUMENTS 2,862,796 12/1958 Gomberg ..................... 431/88

FOREIGN PATENT DOCUMENTS 3643263 of 0000 Germany .
607141 of 0000 U.S.S.R. .
1337777 of 0000 U.S.S.R. .
1573425 of 0000 U.S.S.R. .
1629846 of 0000 U.S.S.R. .

OTHER PUBLICATIONS

F. G. Kost et al. "Handbook on Clinical Laboratory Investigations . . . " 1964, 2 pp. (with translation).
Chemistry for the Health Sciences 1973 pp. 394-395.
V. E. Predtechensky, "Handbook on Clinical Laboratory Investigations" 1964 pp. 427, 444.
Europe Urology, 1989, I6, No. 3, pp. 212-217, Abstract.

Primary Examiner—David A. Redding
Attorney, Agent, or Firm—Ladas & Parry

[57] ABSTRACT

A method of diagnosing complicated urolithiasis consists in testing for and finding the presence of albumen in a urine sample. A portion of said sample is dried and a crystallographic study is performed. On finding a marginal amorphous area, accommodating a central crystalline area, pyelonephritis is diagnosed. On discovering a full crystalline area (i.e. with no marginal amorphous area), calculous pyelonephritis is diagnosed.

The method of prognostication involves testing for and finding the absence of albumen in a urine sample. A portion of the urine sample is mixed with a 8-12% protein solution, the mixture is then dried and a crystallographic study is conducted. With a full non-transparent crystallization of the sample (i.e. without the marginal amorphous area), urolithiasis is prognosticated.

3 Claims, 1 Drawing Sheet

METHODS OF DIAGNOSING COMPLICATED UROLITHIASIS AND PREDICTING UROLITHIASIS

This is a continuation of copending application(s) Ser. No. 07/895,324 filed on Jun. 8, 1992 now abandoned which is a continuation of International Application PCT/SU91/00140 filed on Jul. 9, 1991.

FIELD OF THE INVENTION

The invention relates to medicine, more specifically, to methods of diagnosing complicated urolithiasis and prognosticating same.

At present for purposes of diagnosing said urolithiasis, particularly pyelonephritis, calculous pyelonephritis, use is made of clinical laboratory examination of urea, the X ray and ultrasound analysis of kidneys and urea excretory tracts.

A possibility of the onset of urolithiasis is evaluated if risk factors are available such as hereditary predisposition and endemicity.

BACKGROUND ART

Known in the art is a method of diagnosing pyelonephritis based on laboratory methods of investigations one of which is determination of the contained albumen in urea. The method is based on coagulation of the albumen with chemical reagents, for example, nitric acid, sulfosalicylic acid, to mention only a few; and physical methods, particularly, heating said urea etc (Spravochnik po klinicheskim laboratornym metodam issledovaniya. Edited by E. Kost, Moscow, MEDITSINA Publishers, 1975; Laboratornye metody issledovaniya v klinike. Spravochnik, edited by V. Menshikov, Moscow, MEDITSINA Publishers, 1987).

Also known is a method for the examination of a urea sample containing albumen which is based on crystallography. This method can also be used for diagnosing pyelonephritis. It consists in the following: a sample from the top layer of settled urea is applied to a microscope slide to be dried to complete crystallization and the presence of albumen is established in the urea under examination, when a marginal amorphous area shows itself. Along with this, glucose is found in the urea if a crystallization area is absent altogether (SU, A1, 1573425).

Known in the art is a method for diagnosing ureteral calculus disease which is based on finding calculus formation in cases where a precipitate is observed in freshly excreted urine or a short while after urination (V. Predtechensky "Rukovodstvo po klinicheskim laboratornym issledovaniya", MEDITSINA, 1964, pp.420–446). Such examinations are performed in native urea. In order to slow down evaporation and desiccation, a urine sample is covered with cover glass.

Also known is a method for prognosticating urolithiasis according to which determination is given to a degree of risk of calcium phosphate crystallization in urine by counting the formed crystals of specific size according to mathematical calculations with account taken of certain factors ("Urological Research", N 2, 15, 1987, Springer-Verlag, H.-G. Tiselius "Measurement of the Risk of Calcium Phosphate Crystallization in Urine", s.79–81).

Also known is a method for prognosticating urolithiasis which allows for a combined calculation of the morphological parameters of a cuppelvic system with the clinical-chemical parameters of urine on the basis of a discriminant analysis with consideration of eight functions for 3–10 parameters ("European Urology", 16, N 3, 1989, S. Karger A. G. Basel; E. Schultz, R. Boerner, P. Brundig, F. Maeurer "Influence of Different Factors on the Formation of Calcium Oxalate Stones", s.218–222).

DISCLOSURE OF THE INVENTION

It is the principal object of the present invention to specify the diagnosis of complicated urolithiasis, more specifically, calculous pyelonephritis, and also predict said urolithiasis in healthy persons on examination when urine examination has no deviations from normal and subjective complaints are absent.

This object is accomplished by the claimed new method of diagnosing calculous pyelonephritis. In addition to clinical examination of a urine sample for the presence of albumen, a portion of the urine sample is additionally taken to be applied to the surface of glass, and dried, followed by crystallographic examination. The presence in the dried portion of said sample of a marginal amorphous area, within which the central crystalline area is located, points to the presence of pyelonephritis. If said amorphous area is absent, i.e. inspection reveals a full crystalline area, the diagnosis is calculous pyelonephritis.

The claimed invention makes it possible to obtain a simple method of diagnostics in clinical laboratory practice requiring no X ray or ultrasound examination, a factor that enables one to avoid radiation and ultrasound loading on the patient and also the use of expensive apparatus which is not readily available. The method can well be carried out by a person of skill in the art.

The object of the invention is accomplished by the claimed method for predicting urolithiasis in healthy persons. In addition to the clinical examination of urine samples for absence of albumen, to said urine sample portion is additionally added 8–12% of a protein substance, for example, albumen. A mixture sample is applied to a glass substrate to be dried at room temperature for about a day and crystallographic investigations are performed. If the dried mixture shows a full non-transparent crystallization, i.e. there is observed the absence of the protein amorphous area in the urine/protein mixture, the prognostication is urolithiasis.

Performance of timely diet measurements and medicament therapy with such patients can prevent stone formation. The claimed method contributes to prognosticating urilithiasis in persons having not only hereditary predisposition but also any forms of acquired urolithiasis, i.e. actually 100% of cases.

The method of patent protection sought assures the following advantages: to predict urolithiasis rapidly, without a patient's pre-preparation and without using special equipment and expensive reagents.

The method can be introduced into practice on a wide scale in all medical establishments and provides a possibility of mass-scale examinations during preventive treatment directed to prevention of the progress of ureteral calculus disease.

BRIEF DESCRIPTION OF THE DRAWINGS

The invention is explained by a clear description of its dependent features with reference to the accompanying drawings in which:

TABLE I-continued

Data on patients' clinical-laboratory examination

| No. 1 | Test for calculous pyelonephritis dried urine sample, type 2 | presence of albumin in urine 3 | Discovery of concrements in examin. X ray 4 | Ultrasound 5 | Clinical diagnosis 6 |
|---|---|---|---|---|---|
| 15. | full crystallization | + | yes | yes | calculous pyelonephritis |
| 16. | full crystallization | + | no /X-ray-negative/ | yes | calculous pyelonephritis |
| 17. | full crystallization | + | yes | yes | calculous pyelonephritis |
| 18. | full | + | yes | yes | calculous |
| 19. | full crystallization | + | no /X-ray-negative/ | yes | calculous pyelonephritis |
| 20. | full crystallization | + | yes | yes | calculous pyelonephritis |
| 21. | full crystallization | + | yes | yes | calculous pyelonephritis |
| 22. | full crystallization | + | yes | yes | calculous pyelonephritis |
| 23. | full crystallization | + | yes | yes | calculous pyelonephritis |
| 24. | full crystallization | + | yes | yes | calculous pyelonephritis |
| 25. | full crystallization | + | yes | yes | calculous pyelonephritis |
| 26. | full crystallization | + | yes | yes | calculous pyelonephritis |
| 27. | presence of marginal amorphous area crystalline one in the conter | + | no | no | chronic pyelonephritis |
| 28. | presence of marginal amorphous area and crystalline one in the conter | + | no | no | chronic pyelonephritis |
| 29. | presence of marginal amorphous area and crystalline one in the conter | + | no | no | chronic pyelonephritis |
| 30. | presence of marginal amorphous area and crystalline one in the conter | + | no | no | chronic pyelonephritis |
| 31. | presence of marginal amorphous area and crystalline one in the conter | + | no | no | chronic pyelonephritis |
| 32. | presence of marginal amorphous area and crystalline one in the conter | + | no | no | chronic pyelonephritis |
| 33. | presence of marginal amorphous area and crystalline one in the conter | + | no | no | chronic pyelonephritis |
| 34. | presence of marginal amorphous area and crystalline one in the conter | + | no | no | chronic pyelonephritis |
| 35. | presence of marginal amorphous area and crystalline one in the conter | + | no | no | chronic pyelonephritis |
| 36. | presence of marginal amorphous area and crystalline one in the conter | + | no | no | chronic pyelonephritis |

By way of control, a portion of urine is applied parallel with a sample, without adding an albumen substance. The thus dried mixture of said urine and albumen solution are subjected to visual crystallographic examination.

In conclusion, a correlation is made of the observable patterns of crystallization of a urine mixture sample for the presence of central and marginal areas.

EXAMPLE 3

Patient S. On crystallographic examination of a mixture of urine and albumen solution, there are visually found two areas: in the center—a crystallization area, on the margin—a transparent amorphous area. A negative qualitative reaction for albumen is found.

Conclusion: no prognostication of urolithiasis.

Figure 1:
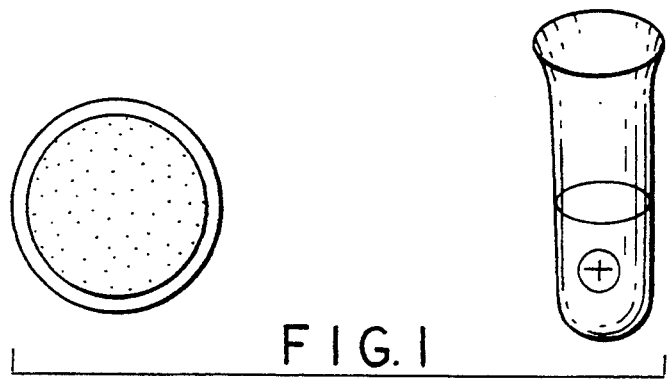
Figure 2:
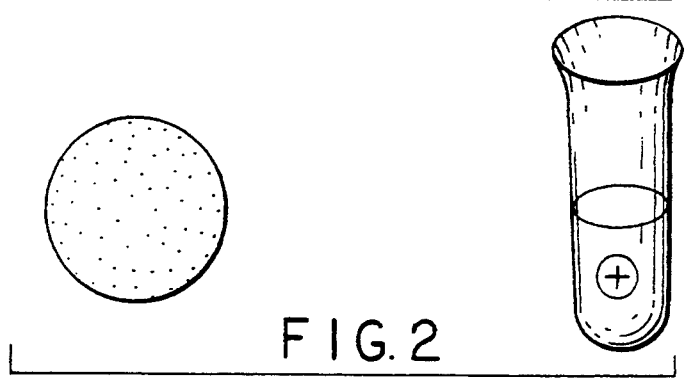
Figure 3:
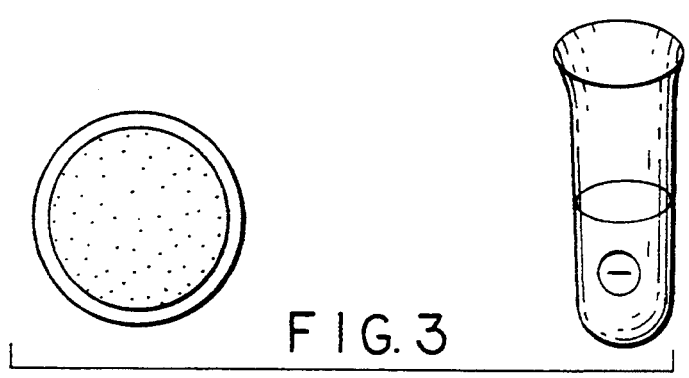

Clinical diagnosis: right kidney prolapse (see FIG. 3).

EXAMPLE 4

Patient D. On crystallographic examination of a mixture of urine and albumen solution there is visually discovered one area that is completely crystallized.

Conclusion: urolithiasis is predicted.

Figure 4:
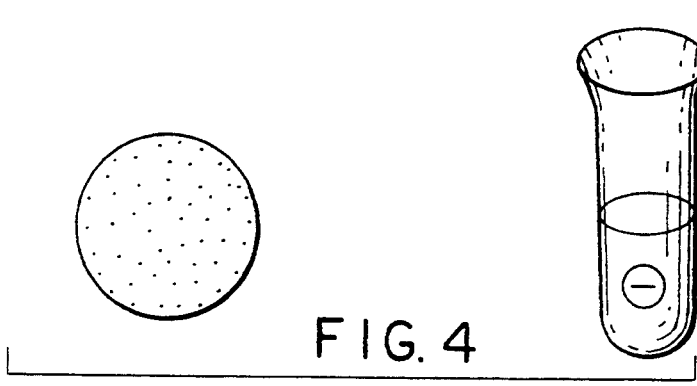

Clinical diagnosis: nephritis (see FIG. 4).

It is worthy to note that in the two-above-described Examples 3 and 4, the control samples provided one and the same picture, namely, one completely crystallized area, i.e. no result has been yielded as regards prediction of the disease.

The claimed method enables one to prognosticate urolithiasis in healthy persons and to take measures towards preventing stone formation. The method is simple, and easy to implement.

The method was checked on 1088 practically healthy people. Results are given in Tables 2 and 3.

ing out preventive treatment directed to prevention of the progress of urolithiasis.

We claim:

1. A method for diagnosing pyelonephritis of a non-calculous origin by examination of a urine sample comprising separating the urine sample into at least two portions, testing a first of said two portions for presence of albumen, drying a second of said portions so that it crystallizes, and examining for the presence of a marginal amorphous area in the dried crystallized second portion.

2. A method for diagnosing calculous pyelonephritis by examination of a urine sample comprising separating the urine sample into at least two portions, testing a first of said at least two portions for presence of albumen, drying a second of said portions so that it crystallizes and examining for absence of a marginal amorphous area in the dried crystallized second portion.

3. A method for predicting urolithiasis by examination of a urine sample comprising separating the urine sample into at least two portions, screening a first of said portions for the absence of albumen, mixing the second portion with an 8–12% albumen solution, drying the resultant mixture at room temperature for about a day and screening to detect whether there is substantially complete crystallization.

TABLE 2

Results of examination of practically healthy persons

| Total Number | Number of people — no prognosis urolithiasis | Number of people — prognosis urolithiasis | Concrements found in USI* of 84 persons in whom no urolithias was prognosticated — yes | Concrements found in USI* of 84 persons in whom no urolithias was prognosticated — no | Concrements found in USI of 24 persons in whom urolithiasis was prognosticated — yes | Concrements found in USI of 24 persons in whom urolithiasis was prognosticated — no | Concrements found in USI 22 months after observation of: 84 persons with no urolithiasis prognosis — yes | 84 persons with no urolithiasis prognosis — no | 15 persons with urolithiasis prognosis — yes | 15 persons with urolithiasis prognosis — no |
|---|---|---|---|---|---|---|---|---|---|---|
| 108 | 84 | 24 | 0 | 84 | 9 | 15 | 0 | 84 | 7 | 8 |
| 100% | 77.8% | 22.2% |   | 100% | 37.5% | 62.5% |   | 100% | 46.7% | 53.3% |

*ultrasound inspection

TABLE 3

Results of examination of 15 persons with the prognosis of urolithiasis according to the claimed method
Presence /+/ or absence(−) of concrements in kidneys, urine tracts on the basis of USI

| N | at the moment of prognostication | 6–8 month after | 12–14 months after | 18 months after | 22 months after |
|---|---|---|---|---|---|
| 1. | − | + | +* | + | + |
| 2. | − | + | + | + | + |
| 3. | − | − | + | + | +* |
| 4. | − | − | + | + | + |
| 5. | − | − | − | + | + |
| 6. | − | − | − | − | + |
| 7. | − | − | − | not performed | +* |
| 8. | − | − | − | − | − |
| 9. | − | − | − | − | − |
| 10. | − | − | − | − | − |
| 11. | − | − | − | − | − |
| 12. | − | − | − | − | − |
| 13. | − | − | − | − | − |
| 14. | − | − | − | − | − |
| 15. | − | − | − | − | − |

*a fit of kidney colic was recorded.

Industrial applicability

The invention may find a variety of applications in the practice of all medical establishments as not requiring expensive facilities and reagents. Its advisable to put this invention into practice during mass-scale prophylactic examinations of population for purposes of carry-

* * * * *